(12) United States Patent
Novosad et al.

(10) Patent No.: US 11,754,648 B2
(45) Date of Patent: Sep. 12, 2023

(54) FERROMAGNETIC PARTICLES AS ULTRA-SENSITIVE NON-LINEAR RESPONSE LABELS FOR MAGNETIC PARTICLES IMAGING (MPI) AND SENSING APPLICATIONS

(71) Applicant: UCHICAGO ARGONNE, LLC, Chicago, IL (US)

(72) Inventors: Valentine Novosad, Lemont, IL (US); Elena A. Rozhkova, Lemont, IL (US); Maxim Nikitin, Lemont, IL (US); Petr Nikitin, Lemont, IL (US)

(73) Assignee: UChicago Argonne, LLC, Chicago, IL (US)

( * ) Notice: Subject to any disclaimer, the term of this patent is extended or adjusted under 35 U.S.C. 154(b) by 106 days.

(21) Appl. No.: 17/156,796

(22) Filed: Jan. 25, 2021

(65) Prior Publication Data
US 2021/0255257 A1 Aug. 19, 2021

Related U.S. Application Data

(62) Division of application No. 15/677,971, filed on Aug. 15, 2017, now Pat. No. 10,901,051.

(51) Int. Cl.
| *A61B 5/00* | (2006.01) |
| *G01R 33/12* | (2006.01) |
| *A61B 5/0515* | (2021.01) |
| *A61K 49/18* | (2006.01) |

(52) U.S. Cl.
CPC ........ *G01R 33/1269* (2013.01); *A61B 5/0515* (2013.01); *A61K 49/1806* (2013.01); *A61K 49/1818* (2013.01); *G01R 33/1276* (2013.01)

(58) Field of Classification Search
CPC combination set(s) only.
See application file for complete search history.

(56) References Cited

U.S. PATENT DOCUMENTS

| 8,854,871 B1 | 10/2014 | Jain et al. |
| 2006/0248944 A1 | 11/2006 | Gleich et al. |
| 2009/0004758 A1* | 1/2009 | Park ................. G01N 33/54373 436/526 |

(Continued)

FOREIGN PATENT DOCUMENTS

| EP | 1 262 766 B1 | 11/2009 |
| RU | 2166751 C1 | 5/2011 |

(Continued)

OTHER PUBLICATIONS

Ade & Stoll, "Near-edge X-ray absorption fine-structure microscopy of organic and magnetic materials," Nature Materials 8, pp. 281-290 (2009).

(Continued)

*Primary Examiner* — Joel F Brutus
(74) *Attorney, Agent, or Firm* — Foley & Lardner LLP (57) ABSTRACT

A significant enhancement of detection capabilities of the room temperature MPQ is seen using optical lithography-defined, ferromagnetic iron-nickel alloy microdisks. Irreversible transitions between strongly non-collinear (vortex) and a collinear single domain states, driven by an ac magnetic field, translate into a nonlinear magnetic response that enables ultrasensitive detection of material at relatively small magnetic fields.

20 Claims, 7 Drawing Sheets

(56) References Cited

U.S. PATENT DOCUMENTS

| | | | |
|---|---|---|---|
| 2010/0188075 A1* | 7/2010 | Litvinov | G01N 33/54373 252/62.51 R |
| 2010/0260984 A1 | 10/2010 | Wu | |
| 2010/0303722 A1* | 12/2010 | Jin | A61L 27/18 623/23.72 |
| 2013/0241548 A1 | 9/2013 | Gleich et al. | |
| 2014/0356877 A1 | 12/2014 | Krishnan et al. | |
| 2015/0168507 A1 | 6/2015 | Terki et al. | |
| 2016/0158387 A1* | 6/2016 | Khnadhar | A61K 41/0052 600/12 |
| 2017/0218167 A1* | 8/2017 | Majidi | C08K 3/08 |

FOREIGN PATENT DOCUMENTS

| | | |
|---|---|---|
| WO | WO-2004/091394 A2 | 10/2004 |
| WO | WO-2016/161162 A1 | 10/2016 |

OTHER PUBLICATIONS

Bontus, et al., "Cardiac MPI of mice over the complete heart cycle," 2009 IEEE Nuclear Science Symposium Conference Record (NSS/MIC), pp. 3999-4000 (2009).

Buchanan, et al., "Soliton-pair dynamics in patterned ferromagnetic ellipses," Nature Physics 1, pp. 172-176 (2005).

Cho, et al., "A magneticswitch for the control of cell death signalling in in vitro and in vivo systems," Nature Materials 11, pp. 1038-1043 (2012).

Dobson, "Remote control of cellular behaviour with magnetic nanoparticles," Nature Nanotechnology 3, pp. 139-143 (2008).

Du, et al., "Design of Superparamagnetic Nanoparticles for Magnetic Particle Imaging (MPI)", International Journal of Molecular Sciences 14(9), pp. 18682-18710 (2013).

Fu, et al., "Protein-Functionalized Synthetic Antiferromagnetic Nanoparticles for Biomolecule Detection and Magnetic Manipulation," Angewandte Chemie 48(9), pp. 1620-1624 (2009).

Ge, et al., "Development of a remanence measurement-based SQUID system with in-depth resolution for nanoparticle imaging," Physics in Medicine & Biology 54(10), pp. N177-N188 (2009).

Gleich, et al., "Experimental results on fast 2D-encoded magnetic particle imaging," Physics in Medicine & Biology 53(6), (2008).

Gleich, et al., "Tomographic imaging using the nonlinear response of magnetic particles," Nature 435, pp. 1214-1217 (2005).

Goodwill, et al., "X-Space MPI: Magnetic Nanoparticles for Safe Medical Imaging," Advanced Materials 24(28), pp. 3870-3877 (2012).

Guslienko, et al., "Magnetization reversal due to vortex nucleation, displacement, and annihilation in submicron ferromagnetic dot arrays," Physical Review B 65, 024414 (2001).

Hu, et al,. "High-Moment Antiferromagnetic Nanoparticles with Tunable Magnetic Properties," Advanced Materials 20(8), pp. 1479-1483 (2008).

Jun, et al., "Chemical design of nanoparticle probes for high-performance magnetic resonance imaging," Angewandte Chemie 47(28), pp. 5122-5135 (2008).

Jun, et al., "Nanoscale size effect of magnetic nanocrystals and their utilization for cancer diagnosis via magnetic resonance imaging," Journal of the American Chemical Society 127(16), pp. 5732-5733 (2005).

Kawagishi, et al., "Detection of fine magnetic particles coated on a thread using an HTS-SQUID," Physica C: Superconductivity 412-414(2), pp. 1491-1495 (2004).

Kim, et al., "Biofunctionalized magnetic-vortex microdiscs for targeted cancer-cell destruction," Nature Materials 9, pp. 165-171 (2010).

Kim, et al., "Mechanoresponsive system based on sub-micron chitosan-functionalized ferromagnetic disks," Journal of Materials Chemistry 21(23), pp. 8422-8426 (2011).

Kim, et al., "Stimuli-Responsive Magnetic Nanomicelles as Multifunctional Heat and Cargo Delivery Vehicles," Langmuir 29(24), pp. 7425-7432 (2013).

Krishnan, "Biomedical Nanomagnetics: A Spin Through Possibilities in Imaging, Diagnostics, and Therapy," IEEE Transactions on Magnetics 46(7), pp. 2523-2558 (2010).

Mannix, et al., "Nanomagnetic actuation of receptor-mediated signal transduction," Nature Nanotechnology 3, pp. 36-40 (2008).

Ney, et al., "Temperature dependent magnetic properties of the GaAs substrate of spin-LEDs," Journal of Physics: Condensed Matter 18(17), (2006).

Nikitin, et al., "Biocomputing based on particle disassembly," Nature Nanotechnology 9, pp. 716-722 (2014).

Nikitin, et al., "Highly sensitive room-temperature method of non-invasive in vivo detection of magnetic nanoparticles," Journal of Magnetism and Magnetic Materials 321 (10), pp. 1658-1661 (2009).

Nikitin, et al., "Magnetic immunoassays," Sensor Letters 5(1), pp. 296-299 (2007).

Nikitin, et al., "New type of biosensor based on magnetic nanoparticle detection," Journal of Magnetism and Magnetic Materials 311(1), pp. 445-449 (2007).

Nikitin, et al., "Quantitative real-time in vivo detection of magnetic nanoparticles by their non-linear magnetization," Journal of Applied Physics 103, 07A304, 3 pages (2008).

Novosad, et al., "Nucleation and annihilation of magnetic vortices in sub-micron permalloy dots," IEEE Transactions on Magnetics 37(4), pp. 2088-2090 (2001).

Orlov, et al., "Magnetic Immunoassay for Detection of Staphylococcal Toxins in Complex Media," Analytical Chemistry 85(2), pp. 1154-1163 (2013).

Orlov, et al., "Rapid dry-reagent immunomagnetic biosensing platform based on volumetric detection of nanoparticles on 3D structures," Biosensors and Bioelectronics 79, pp. 423-429 (2016).

Pankhurst, et al., "Applications of magnetic nanoparticles in biomedicine," Journal of Physics D: Applied Physics 36(13), pp. R167-R181 (2003).

Pankhurst, et al., "Progress in applications of magnetic nanoparticles in biomedicine," Journal of Physics D: Applied Physics 42(22), 224001, 15 pages(2009).

Riehemann, et al., "Nanomedicine—Challenge and Perspectives," Angewandte Chemie 48(5), pp. 872-897 (2009).

Rozhkova, "Nanoscale Materials for Tackling Brain Cancer: Recent Progress and Outlook," Advanced Materials 23(24), pp. H136-H150 (2011).

Rozhkova, et al., "Ferromagnetic microdisks as carriers for biomedical applications." Journal of Applied Physics 105, 07B306, 3 pages (2009).

Shinjo, et al., "Magnetic vortex core observation in circular dots of permalloy," Science 289(5481), pp. 930-932 (2000).

Shipunova, et al., "MPQ-cytometry: a magnetism-based method for quantification of nanoparticle—cell interactions," Nanoscale 8(25), pp. 12764-12774 (2016).

Tay, et al., "Induction of Calcium Influx in Cortical Neural Networks by Nanomagnetic Forces," ACS Nano 10(2), pp. 2331-2341 (2016).

Vitol, et al,. "Microfabricated magnetic structures for future medicine: from sensors to cell actuators," Nanomedicine 7(10), pp. 1611-1624 (2012).

Vitol, et al., "Efficient Cisplatin Pro-Drug Delivery Visualized with Sub-100 nm Resolution: Interfacing Engineered Thermosensitive Magnetomicelles with a Living System," Advanced Materials Interfaces 1(7), 1400182, 9 pages (2014).

Vitol, et al., "Multifunctional Ferromagnetic Disks for Modulating Cell Function," IEEE Transactions on Magnetics 48(11), pp. 3269-3274 (2012).

Wachowiak, et al., "Direct Observation of Internal Spin Structure of Magnetic Vortex Cores," Science 298(5593), pp. 577-580 (2002).

Wang & Li, "Advances in giant magnetoresistance biosensors with magnetic nanoparticle tags: Review and outlook," IEEE Transactions on Magnetics 44(7), pp. 1687-1702 (2008).

Weizenecker, et al., "Three-dimensional real-time in vivo magnetic particle imaging," Physics in Medicine & Biology 52(5), pp. L1-L10 (2009).

(56) References Cited

OTHER PUBLICATIONS

Zabow, et al., "Micro-engineered local field control for high-sensitivity multispectral MRI," Nature 453, pp. 1058-1063 (2008).
Zabow, et al., "Shape-changing magnetic assemblies as high-sensitivity NMR-readable nanoprobes," Nature 520, pp. 73-77 (2015).
Zabow, et al., "The fabrication of uniform cylindrical nanoshells and their use as spectrally tunable MRI contrast agents," Nanotechnology 20(38), 385301, 16 pages (2009).

* cited by examiner

FERROMAGNETIC PARTICLES AS ULTRA-SENSITIVE NON-LINEAR RESPONSE LABELS FOR MAGNETIC PARTICLES IMAGING (MPI) AND SENSING APPLICATIONS

CROSS-REFERENCE TO RELATED APPLICATIONS

This application is a divisional of U.S. patent application Ser. No. 15/677,971, filed Aug. 15, 2017, the content of which is incorporated by reference herein in its entirety.

STATEMENT OF GOVERNMENT INTEREST

This invention was made with government support under Contract No. DE-AC02-06CH11357 awarded by the United States Department of Energy to UChicago Argonne, LLC, operator of Argonne National Laboratory. The government has certain rights in the invention.

FIELD OF THE INVENTION

The present invention relates generally to the field of ferromagnetic particles as ultra-sensitive non-linear response labels for magnetic particles imaging (MPI) and sensing applications.

BACKGROUND

This section is intended to provide a background or context to the invention recited in the claims. The description herein may include concepts that could be pursued, but are not necessarily ones that have been previously conceived or pursued. Therefore, unless otherwise indicated herein, what is described in this section is not prior art to the description and claims in this application and is not admitted to be prior art by inclusion in this section.

Nanoparticles are promising in biology and biomedicine for diverse applications including bio-sensing, imaging, therapy, bio-signaling, and bio-computed theranostic nano-robotics. Magnetic nanoparticles (MP) are an attractive candidate for advancing medical technologies because of their unique functionality, remote control of their magnetization, localization and temperature by external fields, relatively low cost, and environmental friendliness. Magnetic nanoparticles and their (bio)organic hybrids have been proposed for drug delivery, cell sorting, hyperthermia and non-invasive rapid medical imaging applications. When interfaced with a living cell, MPs may be used to manipulate biological machinery and control biological functions at various levels of biosystem complexity—from organelle and single-cell organisms to neural networks and model vertebrate organisms.

Conventionally, MP-based nanolabels have been primarily utilized in magnetic resonance imaging (MM) modality where they enhance contrast due to spatial interaction of their magnetic moments with local water molecules. Another traditionally used imaging technique is superconducting quantum interference device (SQUID) imaging, which requires expensive hardware and may only provide qualitative, non-biocompatible data. Newer techniques such as magnetic particle quantification (MPQ) and magnetic particle imaging (MPI) require direct interaction of the MP with an applied magnetic field. Both MPQ and MPI, which allow for higher precision quantitative mapping without interference from endogenous biological backgrounds, are compatible for in vitro (i.e. immunoassays) and non-invasive in vivo detection. One advantage of magnetic nanoparticles is that they can be directly detected within complex biological environments, i.e. visualized in real time with temporal resolution in vivo within opaque organisms or precisely counted in two-dimensional (2-D) format in complex biological fluids or designed smart bio-robotic devices, with no obscuring background signal from diamagnetic or paramagnetic endogenous materials and molecules. This low-noise method is based on nonlinear magnetization of ferromagnetic material in an oscillating magnetic field.

Currently, detection sensitivity of ferromagnetic materials, i.e. $Fe_3O_4$ nanoparticles, has been limited to approximately 0.33 to 0.4 nanograms (ng) using portable MPQ detectors. Thus, a need exists for improved technology, including development of magnetic labels with tailored properties optimized for stronger signals in MPQ and MPI detection devices.

SUMMARY

One embodiment of the present disclosure relates to a method of fabricating magnetic labels. The method includes (a) depositing a metal-alloy material onto a non-magnetic substrate, (b) patterning the metal-alloy material to form a disk-configuration on the non-magnetic substrate, and (c) applying an external magnetic field to the metal-alloy material to form the magnetic labels, such that after applying the external magnetic field, the magnetic labels irreversibly transition from a spin-vortex (SV) state to a magnetized single-domain (SD) state.

In one embodiment, the method further includes measuring a response of the magnetic labels using magnetic particle quantification (MPQ) or imaging the magnetic labels using magnetic particle imaging (MPI) techniques. In one embodiment, the method further includes detecting the magnetic labels by measuring a frequency harmonics response to the external magnetic field. In one embodiment, the harmonics parameter of the external magnetic field has at least one spectra component of frequency $f_1$ such that $f=(2n+1) \times f_1$, where $n=\pm1, \pm2, \pm3$, etc. In one embodiment, the harmonics parameter of the external magnetic field has two spectral components of frequencies $f_1$ and $f_2$ such that $f=kf_1 \pm mf_2$, where k and m are integers equaling $\pm1, \pm2, \pm3$, etc. and where either k or m may equal 0. In one embodiment, the response of the magnetic labels yields detection of the nanoparticle to at least 39 picograms. In one embodiment, the magnetic labels are microdisks comprising a ferromagnetic iron-nickel alloy core. In one embodiment, the microdisks have diameter (d) to thickness (t) ratios of d/h>2. In one embodiment, a first plurality of the microdisks have a diameter-to-height (d/h) ratio of $2<d/h\le10$, a second plurality of the microdisks have a d/h ratio of $10<d/h\le30$, and a third plurality of microdisks have a d/h ratio of d/h>30.

In one embodiment, the spin-vortex (SV) state includes a non-collinear vortex ground state having zero remanence. In one embodiment, the external magnetic field is an alternating current magnetic field. In one embodiment, the external magnetic field has a magnetic field strength H corresponding to less than 250 Oe. In one embodiment, the external magnetic field operates at frequencies ranging between 100 Hz and 150 kHz. In one embodiment, the magnetic labels have a magneto-crystalline anisotropy less than $10^3$ $J/m^3$ in the plane of the magnetic labels. In one embodiment, the magnetic labels have a magneto-crystalline anisotropy greater than $10^3$ $J/m^3$ and less than $10^6$ $J/m^3$ out of the plane of the magnetic labels. In one embodiment, the magnetic labels are ferromagnetic Fe:Ni permalloy microdisks.

Another embodiment of the present disclosure relates to a method of detecting ferromagnetic nanoparticles. The method includes (a) suspending the ferromagnetic nanoparticles in a buffer solution to form a suspension, (b) providing an magnetic particle quantification (MPQ) detector coil for generating an alternating current (AC) excitation field, (c) placing a mammalian subject inside the MPQ detector coil, (d) retro-orbitally injecting the suspension into a blood flow of a mammalian subject, and (e) detecting distribution of the ferromagnetic nanoparticles in the blood flow in vivo using the MPQ detector coil.

In one embodiment, the method further includes providing a larger coil or set of permanent magnets for generating an external bias direct current (DC) field. In one embodiment, the method further includes applying the external bias DC field concurrently with the AC excitation field prior to the step of detecting the ferromagnetic nanoparticles. In one embodiment, the ferromagnetic nanoparticles are ferromagnetic Fe:Ni permalloy microdisks. In one embodiment, the ferromagnetic nanoparticles in the buffer solution are in an unbound or dispersed state. In one embodiment, a concentration of the ferromagnetic nanoparticles in the buffer solution is $10^8$ to $10^{10}$ microdisks per 1 ml. In one embodiment, the concentration of the ferromagnetic nanoparticles in the buffer solution is $2\times10^9$ microdisks per 1 ml. In one embodiment, the injecting is conducted via an ophthalmic venous sinus injection, tail vein injection, intracranial injection, intraperitoneal injection, subcutaneous injection, or via convection enhanced delivery (CED).

Another embodiment of the present disclosure relates to a method of fabricating ferromagnetic nanolabels. The method includes (a) providing a patterned layer atop a non-magnetic substrate, (b) depositing a metal-alloy material onto the non-magnetic substrate to form metal-alloy disks, (c) lifting off the metal-alloy disks, and (d) re-suspending the metal-alloy disks in a biocompatible solution.

In one embodiment, the patterned layer is obtained by (a1) depositing a coating of a polymer-based light sensitive material, and (a2) patterning the polymer-based light sensitive material using optical lithography or electron-beam lithography, where a thickness of the patterned layer is defined by a thickness of the coating. In one embodiment, the patterned layer is obtained by (a1) depositing a coating of a membrane material, and (a2) patterning the membrane material using stencil lithography, where a thickness of the patterned layer is defined by a thickness of the coating, and where stencil lithography is a resist-less process using a shadow mask stencil to form nano-sized features. In one embodiment, the membrane material includes at least one of silicon, silicon nitride, silicon oxide, or aluminum oxide. In one embodiment, the metal-alloy disks are magnetically silent in absence of external magnetic fields. In one embodiment, the method further includes (e) applying an external magnetic field, where metal-alloy disks irreversibly transition from a non-uniform magnetic state to a uniformly magnetized state. In one embodiment, the non-uniform magnetic state is a spin-vortex (SV) state and the uniformly magnetized state is a single-domain (SD) state.

In one embodiment, the metal-alloy material is deposited by a physical vapor deposition (PVD) process, where the PVD process is selected from the group consisting of thermal evaporation, electron-beam evaporation, atomic layer deposition (ALD), sputter deposition, cathodic arc deposition, and pulsed-electron deposition. In one embodiment, the lifting off is conducted by ultrasound-assisted wet chemistry. In one embodiment, the metal-alloy disks include the metal-alloy material sandwiched between two layers of gold. In one embodiment, the biocompatible solution includes a first plurality of metal-alloy disks having a diameter-to-height (d/h) ratio of $2<d/h\leq10$, a second plurality of metal-alloy disks having a d/h ratio of $10<d/h\leq30$, and a third plurality of metal-alloy disks having a d/h ratio of $d/h>30$.

Additional features, advantages, and embodiments of the present disclosure may be set forth from consideration of the following detailed description, drawings, and claims. Moreover, it is to be understood that both the foregoing summary of the present disclosure and the following detailed description are exemplary and intended to provide further explanation without further limiting the scope of the present disclosure claimed.

BRIEF DESCRIPTION OF THE DRAWINGS

The disclosure will become more fully understood from the following detailed description, taken in conjunction with the accompanying figures, in which:

FIGS. 5A-5C depicts a normalized hysteresis loop for an array of permalloy disks of 1.5-μm diameter measured by a superconducting quantum interference device (SQUID) (circles) and a vibration sample magnetometer (VSM) (crosses) in a magnetic field H parallel to the disk plane for thicknesses at 20 nm (FIG. 5A) and 40 nm (FIG. 5B). The insert in FIG. 5B shows a normalized magnetization curve M(H) with no hysteresis in the magnetic field perpendicular to the disk plane (with the diamagnetic background of the GaAs substrate subtracted).

DETAILED DESCRIPTION

Before turning to the figures, which illustrate the exemplary embodiments in detail, it should be understood that the present application is not limited to the details or methodology set forth in the description or illustrated in the figures. It should also be understood that the terminology is for the purpose of description only and should not be regarded as limiting.

In the present disclosure, optical lithography-defined ferromagnetic Fe:Ni permalloy nanoparticles (i.e. microdisks or disks) having a non-collinear (curled) vortex magnetization ground state are fabricated for magnetic label applications. The non-collinear vortex ground state is characterized by an in-plane, continuously-curling spin configuration with zero net in-plane magnetization in the absence of a magnetic field (zero remanence). Zero-remanence in the disclosed anisotropically-shaped ferromagnetic Fe:Ni permalloy microdisks eliminates magnetically-driven agglomeration when the microdisks interface with a biological system. This feature, along with a high magnetic moment, allows for efficient remote detection, sensing and manipulation of the nanoparticles within biological machinery. Furthermore, these ferromagnetic Fe:Ni permalloy microdisks are detectable based on nonlinear features of their demagnetization process in an alternating (i.e. time-varying) magnetic field. These nonlinear features may be caused by a curled texture of the magnetization such that it is suppressed for any given spatial orientation of the microdisks under application of magnetic fields that are weaker than the alternating magnetic field.

In some embodiments, the ferromagnetic material may include at least one of: Co, Fe, Ni, Fe/Co/B, Fe/B/Si, Co/Ni, Fe/Co/V, Fe/Ni/Mo, Fe/Ni/Zn, Fe/Al/Si, Fe/Pd, Fe/Pt, $Fe_2O_3$, $FeOFe_2O_3$, $NiOFe_2O_3$, $CuOFe_2O_3$, $MgOFe_2O_3$, MnBi, MnSb, $MnOFe_2O_3$, $Y_3Fe_5O_{12}$, $CrO_2$, MnAs, Gd, Tb, Dy, EuO, or a combination thereof. In some embodiments, the disk may include antiferromagnetic materials such as NiO, CoO, Cr, FeMn, FeRh, IrMn, or a combination of thereof. In some embodiments, the ferromagnetic structures may comprise particles, disks, clusters, fibers, wires, sheets, pillars, ribbons, dots, films and single-layer foils. In some embodiments, the ferromagnetic material may be fabricated as core-shell structure comprising a magnetic core and a shell comprising at least one of Au, Ag, Pt, $Al_2O_3$, $SiO_2$, $Si_3N_4$, Ti, $TiO_2$, or a combination thereof.

In some embodiments, a ferromagnetic structure may possess a magneto-crystalline anisotropy less than $10^3$ $J/m^3$ in the plane of the structure and a lateral dimension such that the product of the demagnetizing factor multiplied by the magnetization of saturation is less than the maximum amplitude of the alternating magnetic field. In some embodiments, a ferromagnetic structure may possess a magneto-crystalline anisotropy greater than $10^3$ $J/m^3$ and less than $10^6$ $J/m^3$ out of the plane of the structure. In some embodiments, the anisotropy may be determined from the structure shape, crystalline structure, or interlayer interactions.

The ferromagnetic material may form a portion of an inorganic-bio or nano-bio hybrid material. In some embodiments, the hybrid material may be a nanostructure comprising the ferromagnetic material and at least one of biological structures (i.e. specific targeting proteins and polypeptides, antibodies, and nucleic acids such as aptamers, siRNA or polysaccharides) and organic molecules (i.e. polymers, dyes, drugs) integrated with the nanostructures through chemical bond or via physisorption.

Top-down fabrication of the magnetic structures with non-collinear (curled) vortex magnetization ground states rely on patterning techniques such as ion beam etching, masked plasma etching, electron beam lithography or optical lithography, combined with physical vapor deposition techniques such as cathodic arc deposition, electron beam PVD, evaporative deposition, pulsed laser deposition, and sputter deposition, to produce monodispersed structures having tailored dimensions, composition and magnetic properties. Due to their unique properties, ferromagnetic Fe:Ni permalloy microdisks are used as mediators for controlling cell fate via magneto-mechanical actuation of membranes in weak, oscillating magnetic fields (typically, less than 100 Oe and within frequencies of a few tens of hertz).

An irreversible, AC magnetic field-driven, transition from a strongly non-collinear (curled) vortex ground state to a collinear (single domain) state is described for novel ferromagnetic Fe:Ni permalloy nanoparticles (i.e. microdisks). As a result of this transition, ultra-sensitive MPQ detection may be obtained at relatively weak magnetic fields. In one embodiment, sensitivities of approximately $3.9 \times 10^{-9}$ emu (equivalent to about 39 picograms) of magnetic material have been observed.

Preparation of Ferromagnetic Nanoparticles

A method of fabricating a ferromagnetic nanoparticle includes depositing a metal-alloy material onto a non-magnetic substrate, patterning the metal-alloy material to form a disk-configuration on the non-magnetic substrate, and applying an external magnetic field to the metal-alloy material to form the ferromagnetic nanoparticle. After the step of applying the external magnetic field, the metal-alloy material irreversibly transitions from a spin-vortex (SV) state to a magnetized single-domain (SD) state.

Disk-shaped permalloy (20:80% Fe:Ni alloy) disks were prepared by first depositing the metal-alloy material onto a non-magnetic substrate using physical vapor deposition (PVD) techniques such as cathodic arc deposition, electron beam PVD, evaporative deposition, pulsed laser deposition, and sputter deposition followed by patterning via ion beam etching, masked plasma etching, electron beam lithography or optical lithography. In one embodiment, deposition was conducted via magnetron sputtering and patterning was conducted using optical lithography with a positive tone photoresist, which allows for patterning the microdisks directly on the non-magnetic substrate to achieve a predetermined disk shape and geometry. In one embodiment, gallium arsenide is the preferred substrate because it is readily cleaved into smaller sample size testing pieces without requiring a dicing saw. Alternatively, the substrate may also be comprised of silicon (Si), silicon dioxide ($SiO_2$), aluminum oxide ($Al_2O_3$), sapphire, germanium, alloys of silicon and germanium, indium phosphide (InP), or carbon-based substrate materials (i.e. graphene and diamond). Patterned test permalloy disks fabricated according to the methods described herein are favorable for 2-D magnetic detection model experiments.

In one embodiment, a method of fabricating ferromagnetic nanolabels includes providing a patterned layer atop a non-magnetic substrate, depositing a metal-alloy material onto the non-magnetic substrate to form metal-alloy disks, lifting off the metal-alloy disks, and re-suspending the metal-alloy disks in a biocompatible solution.

In one embodiment, the patterned layer may be obtained by depositing a coating of a polymer-based light sensitive material, and patterning the polymer-based light sensitive material using optical lithography or electron-beam lithography, where a thickness of the patterned layer is defined by a thickness of the coating. In one embodiment, the polymer-based light sensitive material may be a positive photoresist or a negative photoresist. In a positive resist, the resist is exposed with light where the underlying material is to be removed. In positive resists, exposure to the light changes the chemical structure of the resist so that it becomes more soluble in a developer solution. The exposed resist is then washed away by the developer solution, leaving windows of the bare underlying material. Negative tone resists behave in an opposite manner as positive resists. When exposed to the UV light, negative resists becomes crosslinked/polymerized, and more difficult to dissolve in developer. The negative resist remains on the surface of the substrate where it is exposed, and the developer solution removes only the unexposed areas.

In one embodiment, the patterned layer is obtained by depositing a coating of a membrane material and patterning the membrane material using stencil lithography, where a thickness of the patterned layer is defined by a thickness of the coating, and where stencil lithography is a resist-less process using a shadow mask stencil to form nano-sized features. In one embodiment, the membrane material includes at least one of silicon, silicon nitride, silicon oxide, or aluminum oxide. In one embodiment, the metal-alloy disks are magnetically silent in absence of external magnetic fields. In one embodiment, the method further includes applying an external magnetic field, where metal-alloy disks irreversibly transition from a non-uniform magnetic state to a uniformly magnetized state. In one embodiment, the non-uniform magnetic state is a spin-vortex (SV) state and the uniformly magnetized state is a single-domain (SD) state.

In one embodiment, the metal-alloy material is deposited by a physical vapor deposition (PVD) process, including thermal evaporation, electron-beam evaporation, atomic layer deposition (ALD), sputter deposition, cathodic arc deposition, and pulsed-electron deposition. In one embodiment, lifting-off may be conducted by ultrasound-assisted wet chemistry. In one embodiment, the metal-alloy disks include the metal-alloy material sandwiched between two layers of gold. The metal-alloy material may include any combination of materials disclosed herein for ferromagnetic materials. In one embodiment, the biocompatible solution includes a first plurality of metal-alloy disks having a diameter-to-height (d/h) ratio of $2<d/h\leq10$, a second plurality of metal-alloy disks having a d/h ratio of $10<d/h\leq30$, and a third plurality of metal-alloy disks having a d/h ratio of $d/h>30$.

Figure 1:
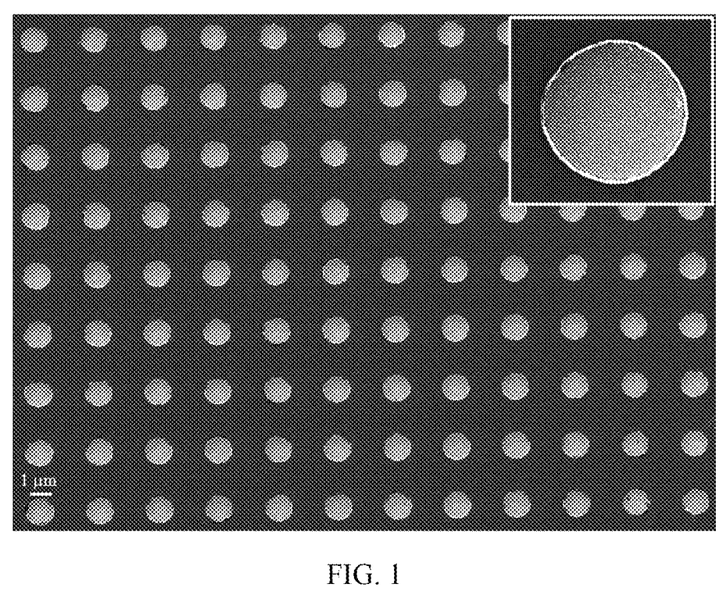
FIG. 1 depicts a scanning electron microscope (SEM) image of 20-nm thick test permalloy disks prepared by optical lithography and magnetron sputtering on GaAs wafers.

FIG. 1 is a scanning electron microscope image depicting the test permalloy disks fabricated according to the methods described herein. Ten-to-forty nanometer (i.e. 20 nm) thick disks having a diameter in the range of 1.0 μm and 2.0 μm (i.e. 1.5 μm) are prepared using optical lithography and magnetron sputtering on GaAs wafers and arranged on a square lattice with a period of 2.0 μm to 3.0 In one embodiment, samples are fabricated on 2-inch wafers and then sectioned into 3×3 mm² slides for characterization. The test permalloy disks are placed into a measuring coil system and exposed to an external, alternating current magnetic field operating at two frequencies, $f_1$ and $f_2$. In one embodiment, $f_1$ operates at frequencies ranging between 100 Hz and 1000 Hz and $f_2$ operates at frequencies ranging between 50 kHz and 150 kHz. The induction response is measured at the combinatorial frequencies F, where $F=f(f_1, f_2)$. The signal-to-noise ratio may be tuned by magnetic field amplitudes and frequencies $f_1$ and $f_2$. In some embodiments, operating frequencies $f_1$ and $f_2$ range between 100 Hz and 150 kHz with magnetic field strengths $H_1$ and $H_2$, respectively, each being less than 250 Oe (i.e. $H_1$<250 Oe and $H_2$<250 Oe). In some embodiments, the applied magnetic fields could be steady, temporal/spatially-varying or combination of thereof Characterization of Ferromagnetic Nanoparticles The magnetic properties of the samples were characterized using magnetic particle quantification (MPQ), a vibration sample magnetometer (VSM), and a superconducting quantum interference device (SQUID).

The magnetic response of the permalloy disk array is measured using two different MPQ devices. The MPQ detection mechanism is based non-linear magnetic response of ferromagnetic nanoparticles subjected to a two-component alternating magnetic field with amplitudes $H_1$ and $H_2$ and frequencies $f_1$ and $f_2$, correspondingly, with signal detection at a combinatorial frequency $F=mf_1\pm nf_2$ (where m and n are integers, one of them can be zero). The first MPQ (MPQ-1) device operated at the following processing conditions:

$$H_1=144\pm10 \text{ Oe},$$

$$H_2=56\pm5 \text{ Oe},$$

$$f_1=154 \text{ Hz, and}$$

$$f_2=150 \text{ kHz}.$$

The signal of this MPQ-1 detector is measured at a combinatorial frequency $F=f_2\pm2f_1$. The maximum field amplitude $H_{max}=H_1+H_2=200\pm15$ Oe of the MPQ-1 device is higher than the saturation fields for all tested permalloy samples. The MPQ-1 detector has a detection limit (0.4 ng) of the most "responsive" commercially available magnetic beads (196-nm Estapor®, Merck Chimie SAS, France) dispersed in 200 μL volume, and a linear dynamic range of greater than seven orders of magnitude. During measurement, the 3×3 mm² characterization slides of test permalloy samples were slowly translated through the MPQ-1 device at a speed of about 150 microns per second. The array's plane was parallel to the direction of the ac magnetic field.

Figure 2:
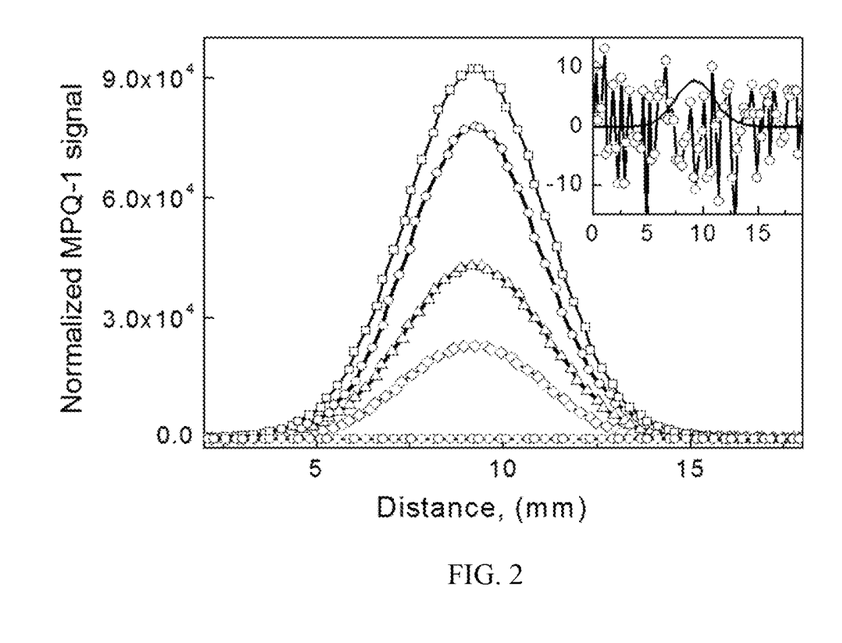
FIG. 2 illustrates the dependence of the MPQ-1 sensor signal (in relative units) vs. slide position for a $3\times3$ mm$^2$ slide comprising an array of the 40 nm (squares), 30 nm (red circles), 20 nm (triangle), 10 nm (diamonds) thick magnetic disks, and for a bare wafer of the same size (magenta circles). Inset: the same dependences for the signal of 30-nm thick disks divided by a factor of $10^4$ (black line) and the noise signal for the unloaded slide (open circles).

FIG. 2 illustrates MPQ-1 sensor's output as a function of the 3×3 mm² slide's lateral position for disk arrays parallel to the direction of the ac magnetic field and having different thicknesses, i.e. 40 nm (squares), 30 nm (red circles), 20 nm (triangle), and 10 nm (diamonds) and for bare wafers of the same size (3×3 mm²) (magenta circles). The signal changes continuously as the slide is displaced and reaches a maximum value when the slide is located in the center of the measurement cell. The signal increases with the volume of the disks (i.e. as the disk thickness increases). The highest signal-to-noise ratio (S/N) in these measurements was achieved for 40 nm thick disks. The noise level was determined using the bare wafer of the same size (FIG. 2 inset). Specifically, as few as 87 particles (i.e. about 39.4 pg) of permalloy, corresponding to a magnetic moment of $3.9 \times 10^{-9}$ emu ($3.9 \times 10^{-12}$, A·m²) may be detected against the background noise. In other words, a detection of 39.4 pg or $3.9 \times 10^{-9}$ emu (87 particles) was obtained at room temperature by using lithography-defined Fe·Ni microdisks with vortex remanence states by the particles nonlinear magnetization at combinatorial frequencies. The detection characteristics of the fabricated ferromagnetic nanoparticle using the processing conditions described herein are at least one order-of-magnitude better than conventional MPQ detection techniques which use commercial superparamagnetic particles. This sensitivity is greater by at least two orders of magnitude than the detection capabilities of SQUID magnetometers designed for extended objects and room-temperature applications. Moreover, SQUID relaxometry is not applicable in vivo and is not sensitive to natural biological background signals.

Figure 3:
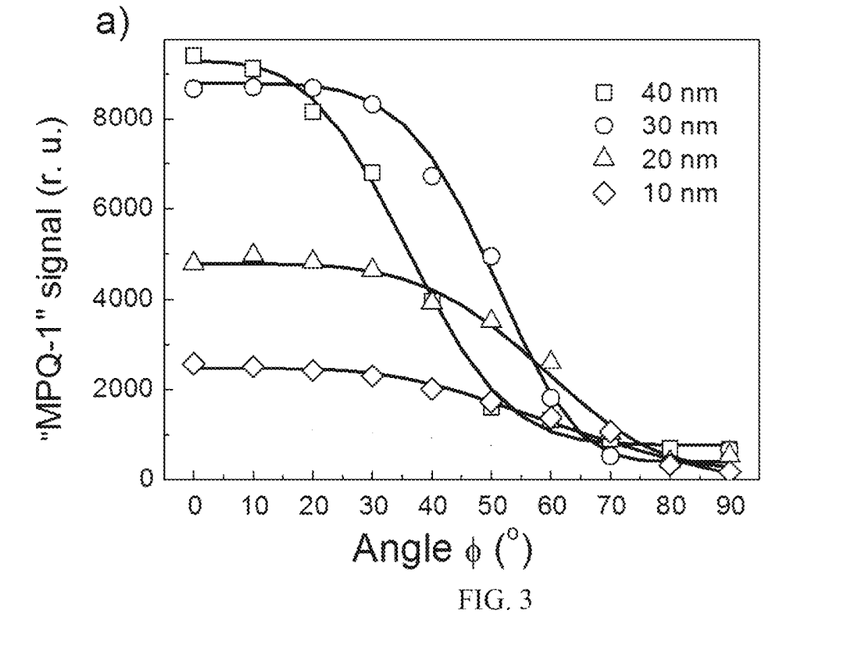
FIG. 3 depicts the angular dependence of the MPQ-1 sensor signal normalized for a 1 mm$^2$ array of 40 nm (squares), 30 nm (circles), 20 nm (triangle), and 10 nm (diamonds) thick magnetic disks.

The disks demonstrated a remarkable dependence of the MPQ signal on the angular orientation; this feature may be used to determine local rheology, which is used for a variety of applications. In realistic biological sensing applications, the disks' angular orientation may be arbitrary and therefore, the disks were positioned in the center of the MPQ-1 sensor at different angles φ with respect to the direction of the alternating current magnetic field. The angle φ was changed by rotating the direction of the ac magnetic field. FIG. 3 compares the angular dependences of the signal S(h, φ) obtained for different disk arrays.

As an initial observation, the normalized MPQ signal increases with the thickness of the magnetic disks. Furthermore, there is no significant angular variation when the angle φ remains small. For example, for a 20 nm thick disk, the signal remains relatively constant at approximately 5000 units at angles φ up to about 30°. Similarly, for a 30 nm thick disk, the signal remains relatively unchanged at approximately 9000 units at angles φ up to about 20°. As misalignment between the applied magnetic field and the disk plane increases, the signal gradually decreases and is minimized as angle φ approaches 90° for all samples. The position of the maximum slope ($\partial S(h, \varphi)/\partial \varphi$) shifts to smaller angles for thicker disks because of an increase of their demagnetizing field $H_D$.

The measured signal is averaged over an oscillation period $1/f_1$ during the total course of the magnetic field application between $H_{max}$ (here, equaling 200±15 Oe). The strongest nonlinearity of M(H) exists only if the vortex nucleation and annihilation processes are involved. Thus, the signal S(h, φ) attains its maximum, when the amplitude of the in-plane component of the applied magnetic field becomes comparable to (or exceeds) the saturation field $H_s$. This explains why for some angles, the signal S(h, φ) is stronger for disks containing less magnetic material (i.e. thinner disks). For example, at an angle of 50°, while it is expected that the signal S(h, φ) is stronger for the 30 nm disk than for the 20 nm disk because the 30 nm disk contains more magnetic material, the signal S(h, φ) for the 20 nm disk is still stronger than that for the 40 nm disk.

Figure 4:
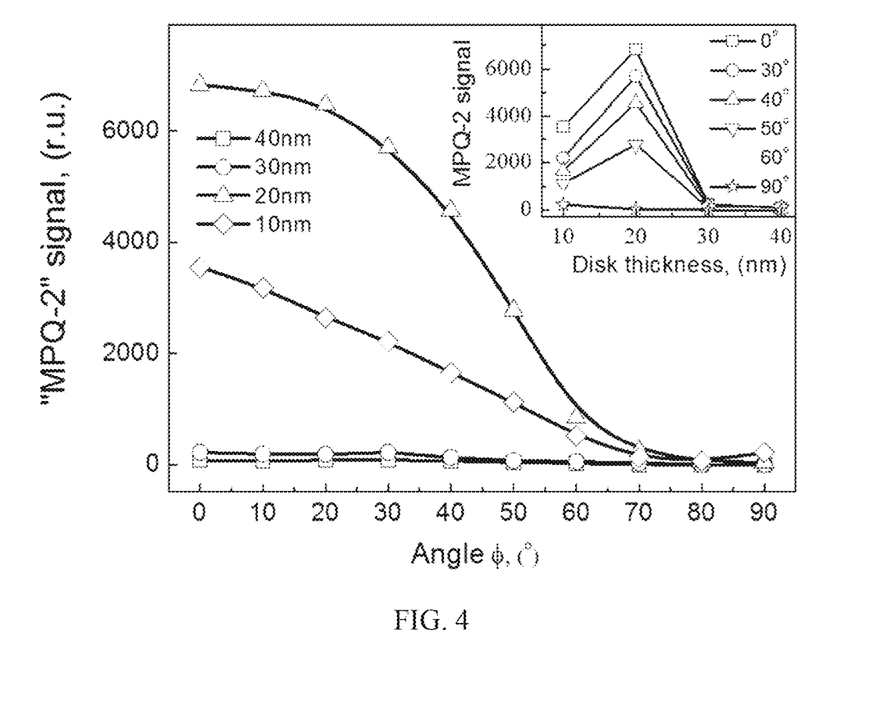
FIG. 4 depicts the angular dependence of the MPQ-2 sensor signal normalized for a 1 mm$^2$ array of 40 nm (squares), 30 nm (circles), 20 nm (up triangle), and 10 nm (diamonds) thick magnetic disks. Inset: Dependence of MPQ-2 sensor signals on disk thickness for different angles φ. Zero degrees is when the disk orientation is parallel to the field of the detection coil.

To further clarify, additional measurements were conducted using a second MPQ (MPQ-2) detector to generate smaller magnetic fields. The data for the MPQ-2 device was collected and analyzed in the same manner as for MPQ-1, except that MPQ-2 operated at the following processing conditions:

$H_1$=64±6 Oe, $H_2$=33±3 Oe, $f_1$=702 Hz, and $f_2$=87 kHz.

The maximum field amplitude $H_{max}$ for MPQ-2 ($H_1$+$H_2$=97±9 Oe) was about half the maximum field amplitude $H_{max}$ for the MPQ-1 detector (200±15 Oe) and substantially less than the saturation fields for the 40- and 30-nm thick disks. As a result, FIG. 4 shows that the 40 and 30 nm thick disks produce nearly zero signal for the entire range of angles. The thinner 20 nm thick disk array generates a strong MPQ response since the maximum field amplitude $H_{max}$ is close to the saturation field $H_S$ for this sample (see the hysteresis loop in FIGS. 5A and 5B below). The inset depicts the dependence of the MPQ-2 sensor signal on disk thickness for different angles φ. Zero degrees is when the disk orientation is parallel to the field of the detection coil.

A key benefit of the disks described herein (i.e. having small geometric aspect ratio h/D) is that they can be detected with relatively weak magnetic fields. This benefit is especially useful for imaging larger, clinically-relevant, objects. As seen in FIGS. 3 and 4, which illustrate the angular dependence of the MPQ-signal S(h, φ), the considerable slope of $\partial S(h, \varphi)/\partial \varphi$ reveals that spin vortex disks can be used as local probes to study various mechanical processes and rheological properties at the nanoscale and in real time. For example, the angular dependence S(h, φ₀) shown in FIG. 3 indicate that while the signal at φ=0° increases monotonously with thickness (i.e. signal for a 40 nm disk is the highest), it has an appreciable maxima at a thickness of 30 nm for angle φ between 30° to 50°, and another maxima at a thickness of 20 nm for angles φ above 60°. Therefore, the immobilization of nanodisks at a fixed angle can be monitored with highest sensitivity for the disks of optimal thickness since angular dependence of the MPQ-signal is characteristic of the disk thickness (for given disk diameter). Thus, signals from disks with different geometries are distinguishable by analyzing the $\partial S(h, \varphi)/\partial \varphi$ derivatives.

In one embodiment, a biofunctionalization process secures the disks in a specific direction, resulting in the signal of the MPQ sensor depending on the direction of the magnetic field generated by the detector. In another embodiment, the biofunctionalization process secures the disks randomly, resulting in an isotropic averaged signal of the MPQ sensor. The functional dependence of the signal S(h, φ) in a rotating magnetic field can be exploited for in vivo imaging (for 3-D tomography).

Figure 5A:
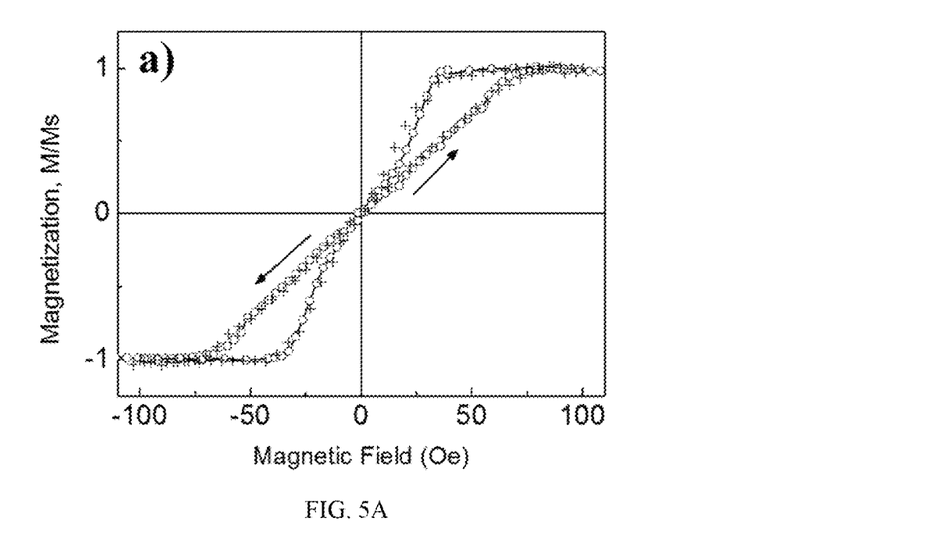
Figure 5B:
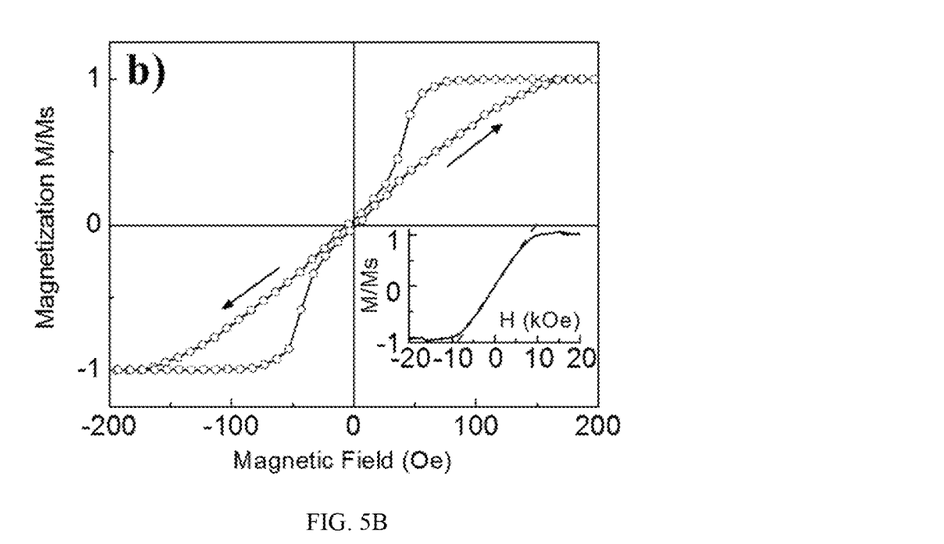
Figure 5C:
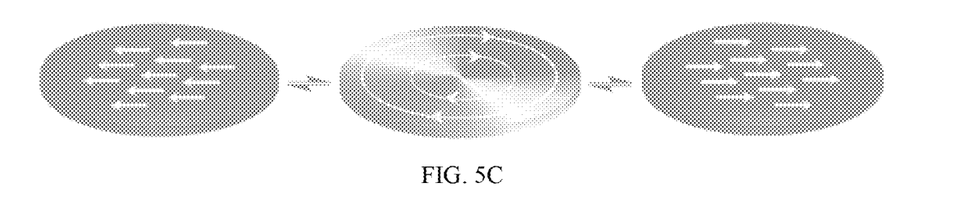
FIG. 5C illustrates net magnetic moments for in remanence samples.

The magnetic properties of the samples were also characterized using a vibration sample magnetometer (VSM) and a superconducting quantum interference device (SQUID). FIGS. 5A-5C depicts a normalized, in-plane hysteresis loop for an array of permalloy disks of 1.5-μm diameter measured by SQUID (circles) and a vibration sample magnetometer (VSM) (crosses) in a magnetic field H parallel to the disk plane for thicknesses at 20 nm (FIG. 5A) and 40 nm (FIG. 5B). The insert in FIG. 5B represents a normalized magnetization curve M(H) with no hysteresis in the magnetic field perpendicular to the disk plane (with the diamagnetic background of the GaAs substrate subtracted). FIG. 5C illustrates net magnetic moments for in remanence samples. In remanence, the samples possess no net magnetic moment, which is indicative of the spin vortex state (central image). In the saturated state the vortex annihilates and the sample becomes uniformly magnetized (left: negative magnetic field; right: positive magnetic field).

In-plane hysteresis loops are typical for vortex nucleation, displacement and annihilation magnetization reversal process, as seen in FIGS. 5A and 5B. As stated above, in remanence, the samples possess no net magnetic moment, which is indicative of the spin vortex (SV) state. Upon application of a small magnetic field, the vortex center is displaced, and the sample gradually becomes magnetized. This corresponds to the linear (reversible) part of the hysteresis loop. When the magnetic field reaches a critical value, $H_S$, the vortex annihilates and the sample saturates to a uniformly magnetized single-domain (SD) phase as schematically depicted in FIG. 5C. In other words, an irreversible transition takes place from the SV state to the SD state when an applied magnetic field exceeds a critical magnetic field $H_s$. Conversely, under decreasing magnetic field the SD phase collapses into SV state, which is accompanied by an abrupt drop in the macroscopic magnetization. Both descending and ascending branches of the hysteresis loop coincide at small fields, when the vortex-core is located close to the center of the disk.

No hysteresis is observed when the magnetic field is applied perpendicular to the disk plane. In this case, the magnetization process corresponds to reversible canting of magnetic moments out of the disk plane. The out-of-plane saturation field is significantly larger than its in-plane saturation field (i.e. $H_S$) counterpart due to the disk geometry. Accordingly, a linear M(H) dependence is observed in a broad field range (see FIG. 5B inset). The shapes of the hysteresis loops in FIGS. 5A and 5B are not affected by a relatively small diamagnetic background from GaAs substrate. The magneto-crystalline anisotropy of permalloy is small compared with magnetostatic demagnetization field, $H_D$, and can be neglected. Subsequently, the in-plane saturation field $H_S$ (the field required for vortex state annihilation) is comparable to $H_D=N_\|\cdot M_S$, where $N_\|$ is the corresponding demagnetizing factor and $M_S$ is the magnetization of saturation (i.e. the critical magnetic field to saturate a material). Both the vortex nucleation $H_N$ field and annihilation $H_{AN}$ field (i.e. the field required for vortex state annihilation; equivalent to in-plane saturation field $H_S$) can be calculated analytically using the "rigid vortex" model. The values of both $H_N$, and $H_{AN}$ increase with increase of the disk geometric aspect ratio (i.e. thickness-to-diameter ratio).

Properties of the Ferromagnetic Nanoparticles

Furthermore, these ferromagnetic Fe:Ni permalloy microdisks are detectable based on nonlinear features of their demagnetization process in an alternating (i.e. time-varying) magnetic field. These nonlinear features may be caused by a curled texture of the magnetization such that it is suppressed for any given spatial orientation of the microdisks under application of magnetic fields that are weaker than the alternating magnetic field.

The ferromagnetic nanoparticles are characterized by non-collinear spin textures that may be suppressed only for certain angular orientations and fixed ranges of the alternating magnetic field. In some embodiments, the ferromagnetic nanoparticles may possess a magneto-crystalline anisotropy less than $10^3$ J/m$^3$ in the plane of the structure and a lateral dimension such that the product of the demagnetizing factor multiplied by the magnetization of saturation is less than the maximum amplitude of the alternating magnetic field. In some embodiments, the ferromagnetic nanoparticles may possess a magneto-crystalline anisotropy greater than $10^3$ J/m$^3$ and less than $10^6$ J/m$^3$ out of the plane of the structure. In some embodiments, the anisotropy may be determined from the structure shape, crystalline structure, or interlayer interactions.

In some embodiments, the ferromagnetic disks have a diameter (d) to thickness (t) ratio of d/h>2. In some embodiments, the ferromagnetic disks have a diameter (d) to thickness (t) ratio of d/h>10. In some embodiments, the ferromagnetic disks have a diameter (d) to thickness (t) ratio of d/h>30. When a magnetic field having at least one spectra component of frequency $f_1$ is applied, the ferromagnetic disks (i.e. particles) exhibit an inductive response that is characterized by even harmonics such that $f=(2n+1)\times f_1$, where n=±1, ±2, ±3, etc. When a magnetic field having two spectral components of frequencies $f_1$ and $f_2$ is applied, the ferromagnetic disks (i.e. particles) exhibit an inductive response that is characterized by combinatorial harmonics such that $f=kf_1\pm mf_2$, where k and m are integers equaling ±1, ±2, ±3, etc. and where either k or m may equal 0.

Biological Application: In-Vivo Studies

For this purpose, 1.5 μm diameter ferromagnetic Fe:Ni permalloy microdisks were lifted off GaAs or SiO$_2$ wafers and re-suspended in phosphate buffered saline (PBS) solution, resulting in concentrations of about $10^8$ to $10^{10}$ (i.e. 2×10$^9$) microdisks per 1 ml. Experiments were conducted to access detectability of the microdisks circulating in the blood flow of mice in real-time using the MPQ technique, as well as to understand how the detector signal can be affected by static magnetic fields. Thus, the in-vivo experimental setup was configured to include an MPQ detector coil generating an excitation (ac) field and a larger coil or set of permanent magnets for providing an external bias (dc) field. An anesthetized mouse was placed inside the MPQ pick-up coil, which quantified the magnetic content passing through the animal's tail veins and arteries. The magnetic microdisks suspended in PBS solution were injected retro-orbitally (i.e. via the ophthalmic venous sinus) into the blood flow of the mouse. In some embodiments, the magnetic microdisks were injected via tail vein injection, intracranial injection, intraperitoneal injection, subcutaneous injection, or convection enhanced delivery (CED).

Figure 6:
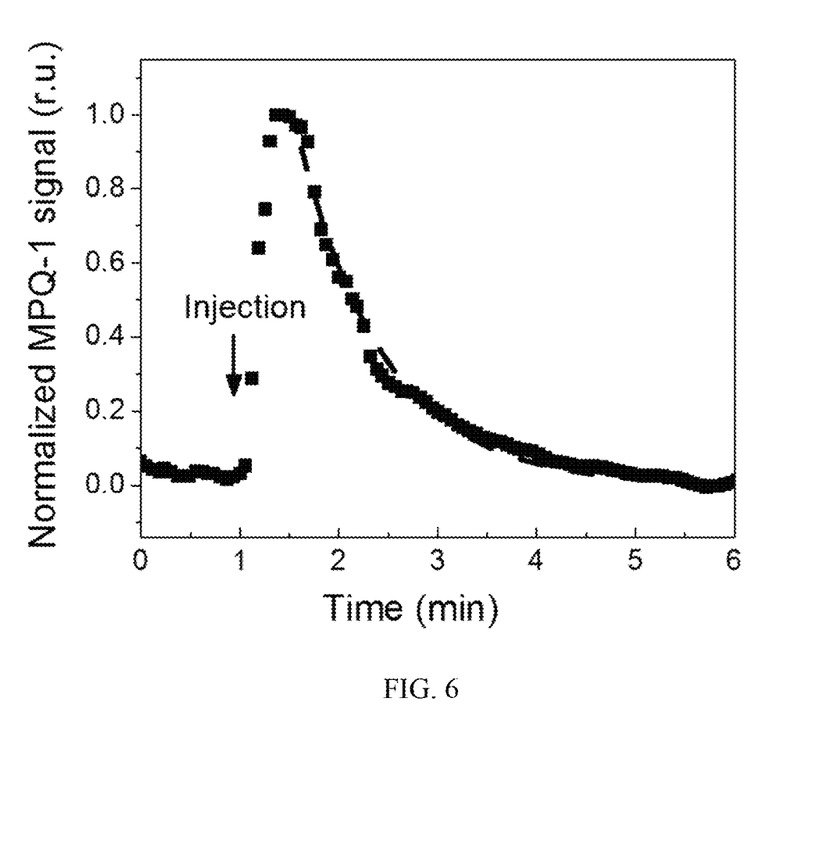
FIG. 6 depicts the dependence of MPQ-1 sensor signals as a function of time and represents blood circulation kinetics of magnetic microdisks in mice. Injection time of the microdisk-containing PBS solution is at approximately one minute and signals are monitored for distribution within the blood volume and clearance.

Initially, blood circulation dynamics of the microdisks were studied without application of an external dc magnetic field. FIG. 6 shows that immediately after injection, the magnetic signal quickly rises as the microdisks reach the tail blood vessels at a maximum concentration, and then exponentially declines as the microdisks are cleared by the reticulo-endothelial system. The microdisks are cleared from the blood stream within less than 10 min. No specific biofunctionalization of the particle's surface was undertaken at this stage in order to allow for a better understanding of the magnetic disk's intrinsic performance and passive distribution in vivo.

Figure 7A:
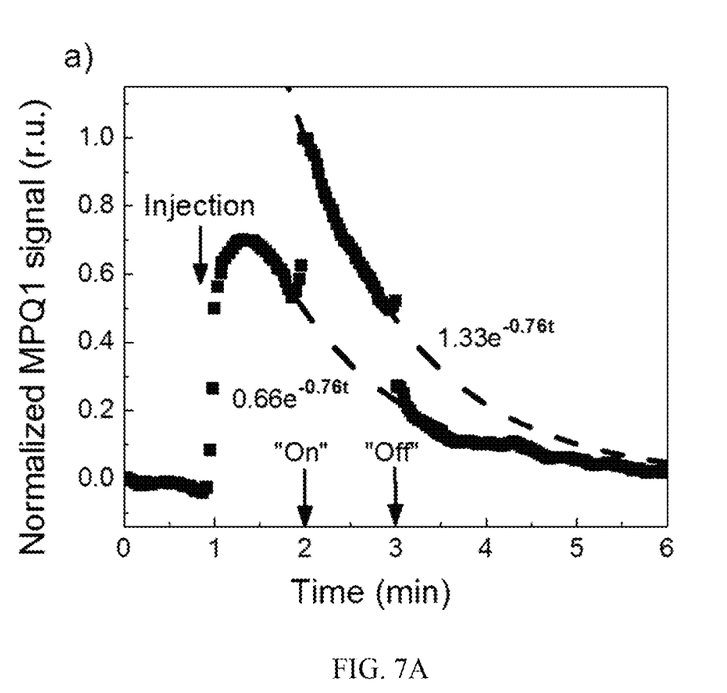
FIG. 7A depicts modulation of the MPQ response of the magnetic microdisks by an external dc field in blood flow in vivo and FIG. 7B depicts the control experiment showing an absence of signal modulation for conventional (non-vortex) magnetic particles.
Figure 7B:
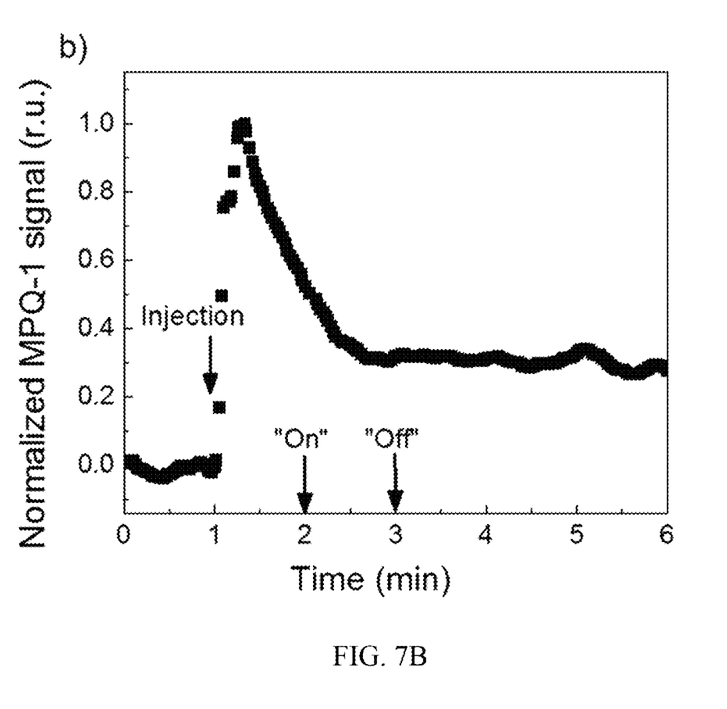

Next, an external dc magnetic field of 15 Oe was applied in addition to the detector's ac field one minute after the microdisks injection. As presented in FIG. 7A, while the kinetics of the particles' clearance remains similar to that of the data presented in FIG. 6, the MPQ signal increases almost two-fold upon application of a small magnetic field, and then abruptly decreases after the field is turned off. Both processes of FIG. 7A are fitted with exponents having the same decay constant, suggesting that the magnetic particle removal rate is not affected by spatially uniform dc magnetic fields. In contrast, commercially-available ~1.0 µm spherical magnetic particles)(Dynabeads®), do not demonstrate any in-vivo signal enhancement in response to an external magnetic field (FIG. 7B). Such responsiveness of the MPQ-signal produced by the microdisks allows for discrimination of the vortex labels from conventional isotropic labels, thereby providing an opportunity to multiplex magnetic assays.

Figure 8:
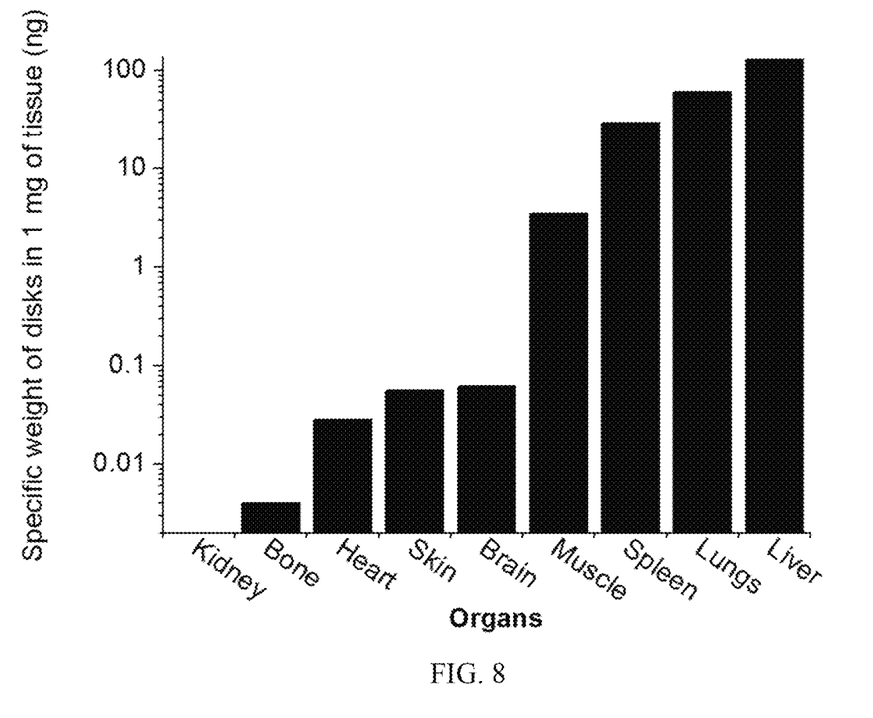
FIG. 8 depicts MPQ-based detection of the microdisks in organs of mice ex vivo after retro-orbital administration of the microdisks.

Next, biodistribution of the magnetic labels was examined ex vivo. The animals were euthanized and different organs were excised, thoroughly washed from traces of blood and then analyzed via MPQ detector. Table 1 indicates that the strongest MPQ signal was detected in the lungs, while significantly weaker signals were detected in the liver and spleen. Signals from other organs, including the brain, were negligible. This data is in agreement with the magnetic resonance imaging (MM) of the whole mouse performed separately and prior to organ extraction. FIG. 8 shows T2-weighted images demonstrating a high concentration of microdisks in the lungs, liver and spleen, with non-detectable uptake by other organs.

TABLE 1

| Organs | MPQ signal, (rel. units) | Microdisk weight normalized to organ mass (ng/mg) |
| --- | --- | --- |
| Brain | 16 | 0.062 |
| Heart | 24 | 0.028 |
| Right kidney | 0 | 0.000 |
| Right thigh bone | 9 | 0.004 |
| Right thigh muscle | 15 | 3.48 |
| Skin | 7 | 0.056 |
| Spleen | 533 | 29.8 |
| Liver | 808 | 131 |
| Lungs | 4865 | 60.5 |

Figure 9:
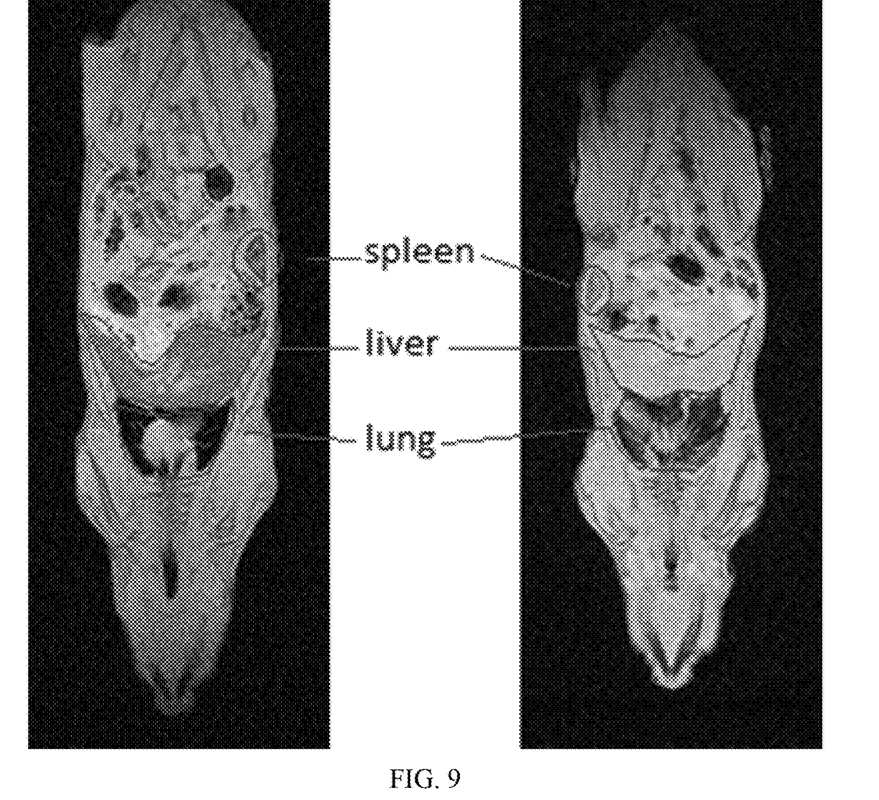
FIG. 9 depicts magnetic resonance imaging (MRI) visualization of the distribution of the magnetic microdisks in a mouse. Contrasting MRI images for the mouse injected with the microdisks (left) is compared with a control mouse without microdisk injection (right). Imaging is conducted in the liver, spleen and lungs; regions having darker color indicate presence of the microdisks.
Figure 10:
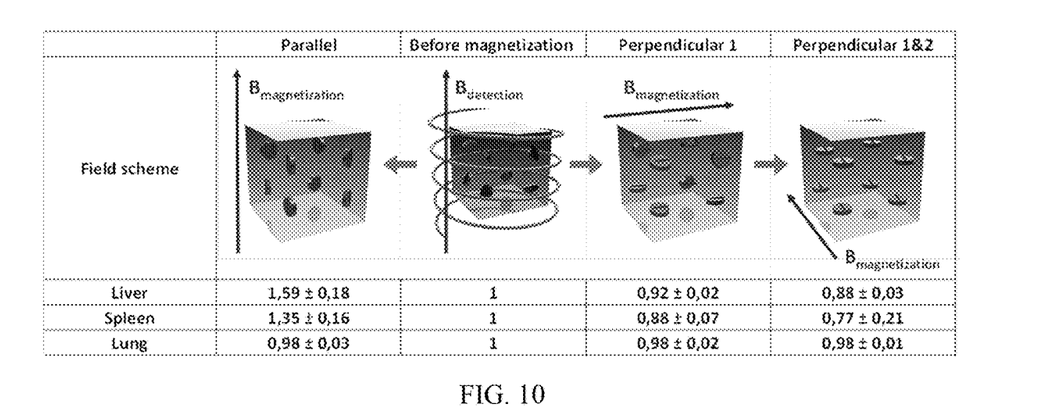
FIG. 10 depicts MPQ-based detection of the rotation of the microdisks within organs (liver, spleen, lungs) of mice-injected with magnetic microdisks. The associated table shows changes in the MPQ-signals of small pieces of each organ (n=3 pieces) after their magnetization with the field oriented (1) parallel to the field of the MPQ detection coil (20 min magnetization), (2) in one perpendicular direction (20 min magnetization) or (3) subsequently in one perpendicular orientation (20 min magnetization) and then in a second perpendicular orientation (20 min magnetization). Magnetization in both perpendicular directions is needed in order to orient all microdisks perpendicular to the field of the detection coil, and thus, is much harder to realize than magnetization in the parallel orientation.

Finally, feasibility of MPQ-based detection of the actuation and manipulation of the microdisks directly in animal tissues was studied. As shown earlier, unlike conventional isotropic nanoparticles, the microdisks feature an angular dependence of their MPQ-signal. Microdisks in tissue samples were magnetized such that physical rotation was observed, thus resulting in a corresponding change in MPQ-signal. FIGS. 9 and 10 show that upon magnetizing the liver, spleen, and lung tissue samples by applying a static magnetic field oriented along the MPQ-coil axis (i.e. along the detecting field), the signal slowly changes over time. Different tissues types exhibit different relative magnitudes of signal change. For example, the signal increases in both the liver (by 59%) and spleen (by 35%) while the signal in the lungs does not change. When the samples are magnetized with the field perpendicular to the detection coil field orientation, the signal decreases for the liver (by about 8%) and spleen (by about 12%) while remaining unchanged for the lungs. Further magnetization of the same samples along the second orientation perpendicular to that of the detection coil further decreases the signals of the liver (a 12% total decrease) and spleen (a 23% total decrease) samples. Combination of MPQ/MPI techniques with microdisk-based labels may explain local micro-rheology of the tissues or the cellular environment in vivo. For instance, while many studies have shown that stiffness of individual diseased (cancerous) cells can differ from healthy ones, performing such analysis in vivo has always been a challenge.

In summary, magnetic nanostructures engineered using top-down techniques are garnering interest in biosensor applications as multispectral MRI contrast enhancement labels, synthetic anti-ferromagnetic particles, and the magneto-resistive sensors for detection of ultralow concentrations of molecular markers. This disclosure demonstrates novel microfabricated magnetic vortex nanomaterials that can be used as advanced ultrasensitive tunable non-linear magnetization labels. Magnetically soft, disk-shaped particles reveal strong nonlinearity of the magnetization process due to irreversible transitions from the spin vortex to single-domain configuration. This feature of the iron-nickel permalloy magnetic dot labels enable a sensitivity of MPQ sensing of $3.9 \times 10^{-9}$ emu or 39 pg of magnetic material. Moreover, detection of these materials was demonstrated in complex biological environments, including ex-vivo isolated organs and in-vivo animal models.

Further optimization may be achieved by using magnetic material with higher saturation magnetization values and tailoring the magnetocrystalline anisotropy. Furthermore, carefully tailoring geometric parameters of the disks or introducing nanoscale interfacial and geometrical defects (i.e. exchange bias, roughness, nano-patterning or texturing) allows for controlling the vortex nucleation and annihilation, as well as vortex-core pinning which enhances the ac magnetic field non-linearity effects in small fields. Desired geometries and magnetic properties of the alloy disks are readily-tunable and tightly-controllable through cost-efficient and scalable micro- and nanofabrication methods. Alloy disks, similar in nature to the permalloy disks used herein, are magnetically silent in absence of external magnetic fields and possess unique size-, geometry- and material-dependent magnetic properties that can be remotely activated using low frequency circuitry. Furthermore, intensive translational studies (i.e. tuning microdisk surface properties to enhance their in vivo stability, blood circulation lifetime, and affinity to sites of disease) may be achieved via biochemical functionalization. Besides detection and imaging in biomedicine, other potential applications include magnetic tagging for anti-counterfeit measures (i.e. drugs, credit cards, currencies, commercial label, secure documents, etc.).

As utilized herein, the terms "approximately," "about," "substantially", and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described and claimed without restricting the scope of these features to the precise numerical ranges provided. Accordingly, these terms should be interpreted as indicating that insubstantial or inconsequential modifications or alterations of the subject matter described and claimed are considered to be within the scope of the invention as recited in the appended claims.

References herein to the positions of elements (i.e. "top," "bottom," "above," "below," "on," etc.) are merely used to describe the orientation of various elements in the FIGURES. It should be noted that the orientation of various elements may differ according to other exemplary embodiments, and that such variations are intended to be encompassed by the present disclosure.

With respect to the use of substantially any plural and/or singular terms herein, those having skill in the art can translate from the plural to the singular and/or from the singular to the plural as is appropriate to the context and/or application. The various singular/plural permutations may be expressly set forth herein for the sake of clarity.

What is claimed:

1. A method of detecting ferromagnetic nanoparticles, the method comprising:
   suspending the ferromagnetic microdisks in a buffer solution to form a suspension, the ferromagnetic nanoparticles have a uniformly magnetized state;
   providing a magnetic particle quantification detector coil for generating an alternating current (AC) excitation field;
   placing a mammalian subject inside the magnetic particle quantification detector coil;
   retro-orbitally injecting the suspension into a blood flow of a mammalian subject; and
   detecting distribution of the ferromagnetic nanoparticles in the blood flow in vivo using the MPQ detector coil.

2. The method of claim 1, further comprising providing a larger coil or set of permanent magnets for generating an external bias direct current (DC) field.

3. The method of claim 2, further comprising applying the external bias DC field concurrently with the AC excitation field prior to the step of detecting the ferromagnetic nanoparticles.

4. The method of claim 1, wherein the ferromagnetic microdisks are ferromagnetic Fe:Ni permalloy microdisks.

5. The method of claim 4, wherein the ferromagnetic nanoparticles in the buffer solution are in an unbound or dispersed state.

6. The method of claim 1, wherein a concentration of the ferromagnetic nanoparticles in the buffer solution is $10^8$ to $10^{10}$ microdisks per 1 ml.

7. The method of claim 6, wherein the concentration of the ferromagnetic nanoparticles in the buffer solution is $2 \times 10^9$ microdisks per 1 ml.

8. The method of claim 1, wherein the injecting is conducted via an ophthalmic venous sinus injection, tail vein injection, intracranial injection, intraperitoneal injection, subcutaneous injection, or via convection enhanced delivery (CED).

9. The method of claim 1, wherein the ferromagnetic nanoparticles's uniformly magnetized state comprises a single-domain (SD) state.

10. The method of claim 1, wherein the ferromagnetic microdisks comprise:
    a first portion having a diameter-to-height ratio of greater than 2 but less than or equal to 10;
    a second portion having a diameter-to-height ratio of greater than 10 but less than or equal to 30; and
    a third portion having a diameter-to-height ratio of greater than 30.

11. A method of fabricating ferromagnetic nanolabels, the method comprising:
    providing a patterned layer atop a non-magnetic substrate;
    depositing a metal-alloy material onto the non-magnetic substrate to form metal-alloy disks;
    applying an external magnetic field to the metal-alloy material, transitioning the metal-alloy material to a uniformly magnetic state;
    lifting off the metal-alloy disks; and
    re-suspending the metal-alloy disks in a biocompatible solution.

12. The method of claim 11, wherein the patterned layer is obtained by:
    depositing a coating of a polymer-based light sensitive material; and
    patterning the polymer-based light sensitive material using optical lithography or electron-beam lithography,
    wherein a thickness of the patterned layer is defined by a thickness of the coating.

13. The method of claim 11, wherein the patterned layer is obtained by:
    depositing a coating of a membrane material; and
    patterning the membrane material using stencil lithography,
    wherein a thickness of the patterned layer is defined by a thickness of the coating,
    wherein stencil lithography is a resist-less process using a shadow mask stencil to form nano-sized features.

14. The method of claim 13, wherein the membrane material comprises at least one of silicon, silicon nitride, silicon oxide, or aluminum oxide.

15. The method of claim 11, wherein the metal-alloy disks, prior to applying the external magnetic field, are magnetically silent in absence of external magnetic fields.

16. The method of claim 11, wherein the non-uniform magnetic state is a spin-vortex (SV) state and the uniformly magnetized state is a single-domain (SD) state.

17. The method of claim 11, wherein the metal-alloy material is deposited by a physical vapor deposition (PVD) process, wherein the PVD process is selected from the group consisting of thermal evaporation, electron-beam evaporation, atomic layer deposition (ALD), sputter deposition, cathodic arc deposition, and pulsed-electron deposition.

18. The method of claim 11, wherein the lifting off is conducted by ultrasound-assisted wet chemistry.

19. The method of claim 11, wherein the metal-alloy disks comprise the metal-alloy material between two layers of gold.

20. The method of claim 11, wherein the biocompatible solution comprises a first plurality of metal-alloy disks having a diameter-to-height (d/h) ratio of $2 < d/h \leq 10$, a second plurality of metal-alloy disks having a d/h ratio of $10 < d/h \leq 30$, and a third plurality of metal-alloy disks having a d/h ratio of $d/h > 30$.

* * * * *